United States Patent
Dolan et al.

[11] Patent Number: 5,518,012
[45] Date of Patent: May 21, 1996

[54] EXPANDED PTFE FLOSS MATERIAL AND METHOD OF MAKING SAME

[75] Inventors: John W. Dolan, Boothwyn, Pa.; Raymond B. Minor, Elkton; John W. Spencer, Jr., Rising Sun, both of Md.

[73] Assignee: W. L. Gore & Associates, Inc., Newark, Del.

[21] Appl. No.: 259,800

[22] Filed: Jun. 15, 1994

[51] Int. Cl.⁶ .................................................. A61C 15/04
[52] U.S. Cl. .................................... 132/321; 132/329
[58] Field of Search ........................ 132/321, 323, 132/329

[56] References Cited

U.S. PATENT DOCUMENTS

| | | |
|---|---|---|
| 3,699,979 | 10/1972 | Muhler et al. . |
| 3,771,536 | 11/1973 | Dragan . |
| 3,830,246 | 8/1974 | Gillings . |
| 3,953,566 | 4/1976 | Gore . |
| 4,029,113 | 6/1977 | Guyton . |
| 4,034,771 | 7/1977 | Guyton . |
| 4,142,538 | 3/1979 | Thornton . |
| 4,270,556 | 6/1981 | McAllister . |
| 4,414,990 | 11/1983 | Yost . |
| 4,776,358 | 10/1988 | Lorch . |
| 4,836,226 | 6/1989 | Wolak . |
| 4,985,296 | 1/1991 | Mortimer, Jr. . |
| 4,996,056 | 2/1991 | Blass . |
| 4,998,978 | 3/1991 | Varum . |
| 5,033,488 | 7/1991 | Curtis et al. . |
| 5,098,711 | 3/1992 | Hill et al. ............................ 132/323 X |
| 5,209,251 | 5/1993 | Curtis et al. . |
| 5,220,932 | 6/1993 | Blass . |
| 5,226,434 | 7/1993 | Britton et al. ........................ 132/321 |
| 5,226,435 | 7/1993 | Suhonen et al. ...................... 132/321 |
| 5,305,768 | 4/1994 | Gross et al. ......................... 132/321 |
| 5,320,117 | 6/1994 | Lazzara et al. ...................... 132/321 |
| 5,340,581 | 8/1994 | Tseng et al. ......................... 424/401 |
| 5,357,989 | 10/1994 | Gathani ................................ 132/321 |

FOREIGN PATENT DOCUMENTS

| | | | |
|---|---|---|---|
| 335466 | 10/1989 | European Pat. Off. ............. 132/321 |
| 2128133 | 4/1984 | United Kingdom ................ 132/321 |
| 2258402 | 2/1993 | United Kingdom ................ 132/321 |
| 9210978 | 9/1992 | WIPO . |

*Primary Examiner*—John G. Weiss
*Attorney, Agent, or Firm*—David J. Johns

[57] ABSTRACT

The present invention is an expanded polytetrafluoroethylene (PTFE) floss with improved handling properties. Unlike previous expanded PTFE flosses, the floss of the present invention employs a fiber of increased thickness so that the floss is maintained in an unfolded orientation. The improved processing steps of the present invention create a floss that has a number of improved properties, including more uniform dimensions along its length, improved compressibility and handling, and automatic visual indication of those segments of the floss that have been used.

27 Claims, 9 Drawing Sheets

EXPANDED PTFE FLOSS MATERIAL AND METHOD OF MAKING SAME

BACKGROUND OF THE INVENTION

1. Field of the Invention

The present invention relates to floss material, and particularly to floss made from expanded polytetrafluoroethylene (PTFE) fibers.

2. Description of Related Art

Since the development of the invention of U.S. Pat. No. 3,953,566 to Gore, flexible fibers made from expanded polytetrafluoroethylene (PTFE) have been used for a variety of purposes, including as a dental floss to clean between teeth. U.S. Pat. No. 4,776,358 to Lorch discloses one such use of an expanded PTFE floss material whereby the floss is folded upon itself to contain active agents. Use of waxed coated expanded PTFE fibers is taught in a number of other patents, including U.S. Pat. Nos. 5,033,488 and 5,209,251 to Curtis et al. U.S. Pat. No. 5,220,932 to Blass discloses use of a non-porous PTFE floss material. Presently there are a number of commercially available expanded PTFE flosses, including those sold under the trademarks GLIDE® by W. L. Gore & Associates, Inc., COLGATE PRECISION® by Colgate Palmolive Company, and EASY-SLIDE by Johnson & Johnson Consumer Products, Inc.

Expanded PTFE flosses have a number of advantages over conventional nylon flosses, including resistance to shredding (and its accompanying sticking of fiber shreds between teeth) and high lubricity. Although existing expanded PTFE flosses are resistant to shredding, unfortunately they still experience a degree of fibrillation. Fibrillation in dental floss is distinguished from shredding in that shredding is considered the breaking off of individual strands of the fiber between teeth, whereas, fibrillation is the splitting of the original fiber to form separate continuous fibers. Both fibrillation and shredding are not desired in a dental floss product. Other problems with expanded PTFE materials is that they tend to be difficult to process and they can have a number of structural problems. For instance, unlike conventional nylon floss that is formed from multiple strands twisted into a fiber with uniform dimensions, expanded PTFE floss materials have been formed from a thin, flat tape slit into single filament strands and then folded prior to the spooling process. This has made expanded PTFE material difficult to control during processing, resulting in a floss with inconsistent width and thickness dimensions along its length. Another concern with expanded PTFE material is that its strength and thinness often produces a floss material that can cut into a user's hands or provide an uncomfortable surface against a user's gums. Finally, it has been believed that leaving thin edges of expanded PTFE floss fiber exposed during flossing may lead to some limited fibrillation.

To address these concerns, commercially available expanded PTFE flosses have one or both of its edges folded upon the floss fiber to increase the thickness of the floss. This process produces a thicker floss without exposed edges, reducing handling and fibrillation problems. Regretfully, such floss material remains difficult to process while maintaining uniform width and thickness dimensions. Furthermore, the folded floss has a tendency to unfold during use, as well as during processing, resulting in a floss material with varying thickness and varying width. Inconsistent thickness is of particular concern since the thickness dimension is believed to be critical for allowing the floss to fill the gap between the teeth for optimal cleaning. Finally, the "feel" of the available PTFE floss material is still wanting both when held by the user and when flossing between teeth.

Accordingly, it is a primary purpose of the present invention to provide an expanded PTFE floss material of uniform dimensions that can be more readily processed.

It is a further purpose of the present invention to provide an expanded PTFE floss material that is more "gripable" and easily handled and used than existing expanded PTFE flosses.

It is still another purpose of the present invention to provide an expanded PTFE floss material that is not folded during processing.

It is yet another purpose of the present invention to provide an expanded PTFE floss with properties presently not available with existing floss materials.

These and other purposes of the present invention will become evident from review of the following specification.

SUMMARY OF THE INVENTION

The present invention comprises an improved expanded polytetrafluoroethylene (PTFE) floss material. The floss of the present invention achieves the necessary dimensions for floss while maintaining an unfolded orientation along its entire length. This is accomplished by employing a relatively thick expanded PTFE sheet that is slit, and optionally further expanded, into the final dimensions of the floss and carefully wound on spools to avoid rolling, folding or bending. Preferably, the floss comprises a minimum, unfolded, thickness of 75 µm and a minimum width of 0.7 mm.

The floss of the present invention has numerous advantages over presently available expanded PTFE flosses. Among the improved properties are: far more uniform dimensions (width and thickness) along its entire length; significantly improved compressibility and, as a result, improved grip ability; and improved handling and comfort during flossing. Additionally, it has been discovered that the floss will densify when passed between teeth during flossing. While the unused floss has an opaque white color, following flossing the length of floss used will densify to a remarkably different transparent or translucent color. This property provides an automatic indication of those areas of floss that have been used. Another improved property of the present invention is its significantly improved fibrillation resistance over conventional expanded PTFE flosses.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved material for use as a floss. As the term "floss" is used herein, it is intended to encompass a thread-like material suitable for use in cleaning between teeth.

The floss of the present invention comprises a single relatively thick strand of expanded polytetrafluoroethylene (PTFE) fiber that is essentially rectangular to oblong in cross-sectional dimensions and is formed substantially without folds or creases. In order to form the floss without folding one or both of its edges over itself, as is required with existing flosses, it is particularly important that the floss of the present invention is formed to have a significantly greater thickness dimension than presently available PTFE floss fibers. For example, prior to folding, conventional expanded PTFE floss fiber sold under the trademark GLIDE® by W. L. Gore & Associates, Inc., has typical dimensions of about 40 μm in thickness and about 2 mm in width. When this material is folded and packaged as dental floss, the material typically has dimensions of about 90 μm in thickness and about 1.2 mm in width. The PTFE floss sold under the name EASY SLIDE by Johnson & Johnson has typical unfolded dimensions of about 23 μm in thickness and about 2.3 mm. When this material is folded and packaged as dental floss, the material typically has dimensions of about 75 μm in thickness and about 1.3 mm in width.

Figure 1:
FIG. 1 is a scanning electron micrograph (SEM) of a cross-section of a floss fiber of the present invention enlarged 90 times.
Figure 2:
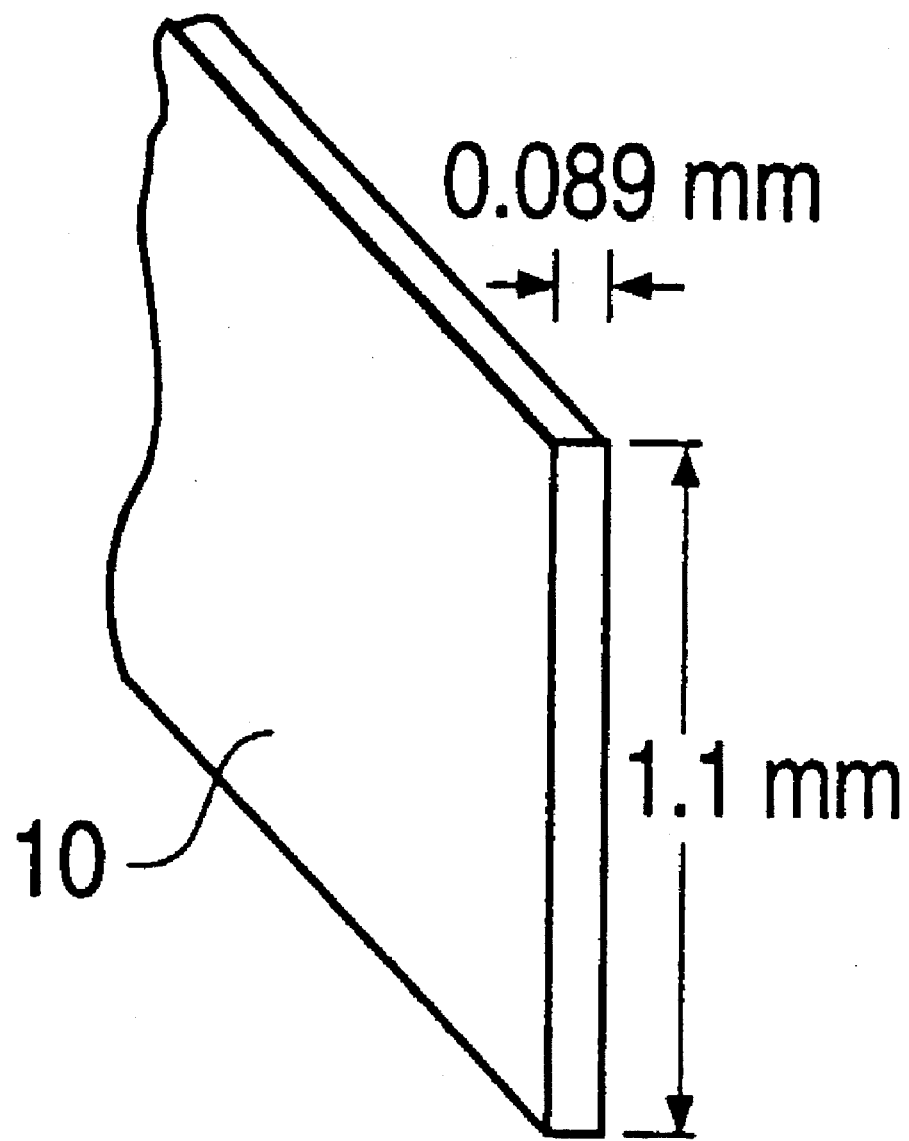
FIG. 2 is a three-quarter isometric view of a floss fiber of the present invention.

As is shown in FIGS. 1 and 2, the floss 10 of the present invention forms essentially a rectangular to oblong cross-sectional dimension. Typical dimensions comprise about 50 to 250 μm, and preferably 75 to 150 μm, in thickness and about 0.5 to 3 mm, and preferably 0.7 to 1.5 mm, in width. The substantial thickness of this material allows the floss to function extremely well without need for folding or otherwise bulking the height of the material. Additionally, the fiber's rectangular to oblong cross-sectional shape is similar to that obtained by the best of the present commercial flosses, but, again, without folding.

Unexpectantly, the floss of the present invention has proven to be highly resistant to fibrillating along its edges during use. The elimination of this fibrillation problem is an important advancement over previous expanded PTFE floss materials, where one of the purposes of folding was to reduce the number of exposed edges on the floss' outer surface subject to fibrillation. As the term is used herein, "outer surface" is defined as the unfolded or uncreased surface which can be seen when exposed to ambient light as the fiber is rotated 360° around the fiber's center line which runs along the length of the fiber.

The floss fiber of the present invention is produced through a series of unique processing steps. First, an expanded PTFE sheet is acquired or formed. Such material is available in a variety of forms from a number of commercial sources, such as from W. L. Gore & Associates, Inc., Elkton, Md., under the trademark GORE-TEX®. This material may be formed as taught in U.S. Pat. No. 3,543,566 to Gore, incorporated by reference. The preferred sheet comprises a thickness of about 0.5 to 1.0 mm; a density of about 0.8 to 1.5 g/cc; and a tenacity of about 0.5 to 1.0 g/tex.

Each of these properties are measured in a conventional manner. Width and thickness is determined through any conventional means, such as through the use of calipers or through measurements through a scanning electron microscope. Density is determined by dividing the measured weight of the sample by the computed volume of the sample. The volume is computed by multiplying the measured length, width, and thickness of the sample. Tenacity is calculated by dividing the sample's tensile strength by its normalized weight per unit length (tex [grams/1000 meters] or denier [grams/9000 meters]).

This sheet may then be slit into strands by passing the sheet through a series of gapped blades set 0.5 to 20 mm apart. After cutting, the fibers may be subjected to a further heat treatment and/or expansion step, such as through the processes discussed below. Finally, the fibers should be wound onto a spool with care taken to avoid rolling or folding of the fibers during the spooling process.

Preferably, an expanded PTFE sheet is formed and slit into fibers of the present invention in the following manner. A fine powder PTFE resin is blended with a lubricant, such as odorless mineral spirits, until a compound is formed. The volume of lubricant used should be sufficient to lubricate the primary particles of the PTFE resin so to minimize the potential of the shearing of the particles prior to extruding.

The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications a reduction ratio of 75:1 to 100:1 is preferred.

The lubricant may then be removed, such as through volatilization, and the dry coherent extrudate is expanded in at least one direction about 1.1 to 50 times its original length (with about 1.5 to 2.5 times being preferred). Expansion may be accomplished by passing the dry coherent extrudate over a series of rotating heated rollers or heated plates.

Once this sheet is formed, the sheet may be formed into a fiber by slitting the dry coherent expanded extrudate into predetermined widths by passing it between a set of gapped blades or other cutting means. Following cutting, the slit coherent extrudate may then be further expanded in the longitudinal direction at a ratio of 1:1.1 to 50:1 (with 15:1 to 35:1 being preferred) to form a fiber. Finally, this fiber may be subjected to an amorphous locking step by exposing the fiber to a temperature in excess of 342° C.

The width of the fiber can be controlled by several process variables known in the art of expanding PTFE. Variables which can affect the width of the fiber are: slit width, expansion temperatures and expansion ratio.

The final dimensions of the fiber should comprise: a width of about 0.5 to 3.0 mm; a thickness of about 50 to 250 μm; a weight/length of about 80 to 450 tex; a density of about 1.0 to 1.9 g/cc; a tensile strength of about 1.5 to 15 kg; and a tenacity of about 10 to 40 g/tex.

Again, these measurements were made in a conventional manner. Bulk tensile strength was measured by a tensile tester, such as an INSTRON Machine of Canton, Mass. In the case of sheet goods, the INSTRON machine was outfitted with clamping jaws which are suitable for securing the sheet goods during the measurement of tensile loading. The cross-head speed of the tensile tester was 25.4 cm per minute. The gauge length was 10.2 cm. In the case of fibers, the INSTRON machine was outfitted with fiber (horn type) jaws that are suitable for securing fibers and strand goods during the measurement of tensile loading. The cross-head speed of the tensile tester was 25.4 cm per minute. The gauge length was 25.4 cm.

Figure 3:
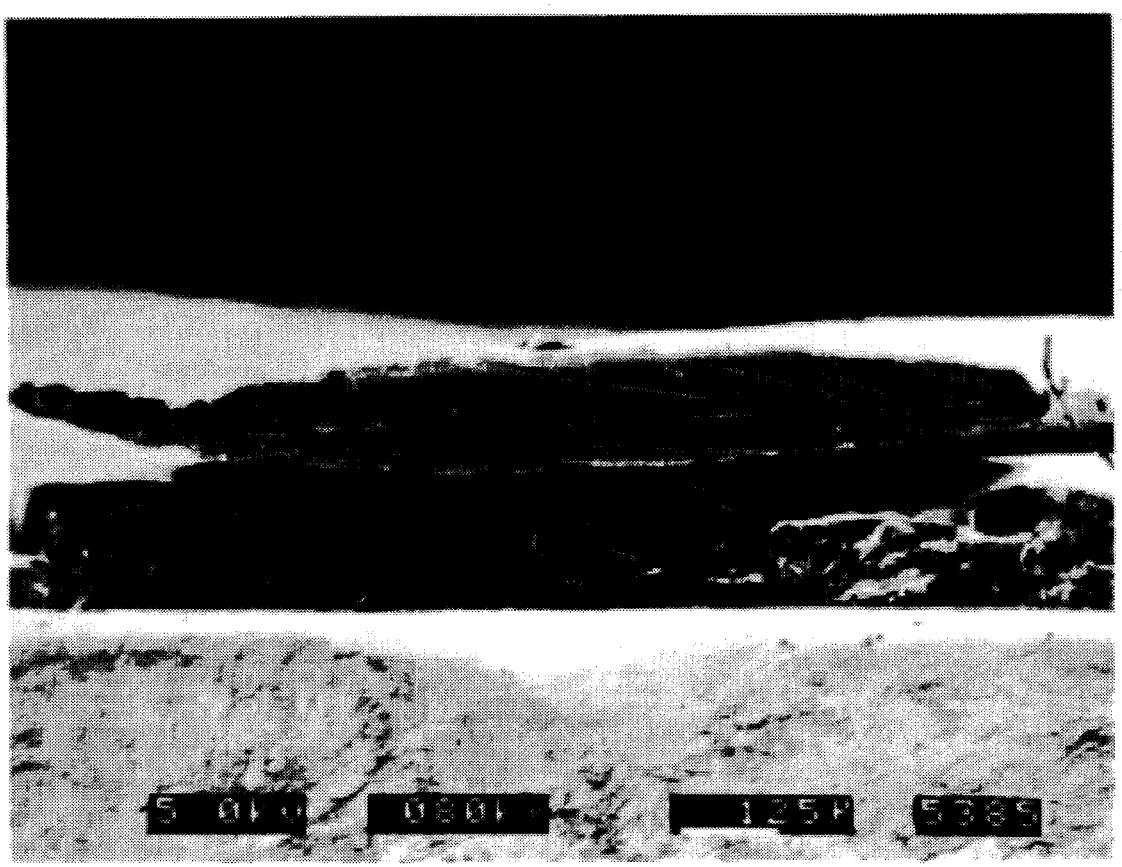
FIG. 3 is an SEM of a cross-section of one commercially available floss fiber enlarged 80 times.

The properties of a floss fiber made in accordance with the above procedures differ considerably from previous PTFE and expanded PTFE flosses. A conventional porous expanded PTFE floss sold under the trademark GLIDE® is shown in FIG. 3. This fiber performs very well as a floss, but, as can be seen in this SEM, the floss is folded upon itself in order to produce sufficient thickness for adequate cleaning and grip ability and to reduce the number of exposed edges hence minimizing the chance of fibrillation. This folding process is difficult to execute and maintain consistently and, as is explained in greater detail below, constrains the properties of the floss.

Figure 4:
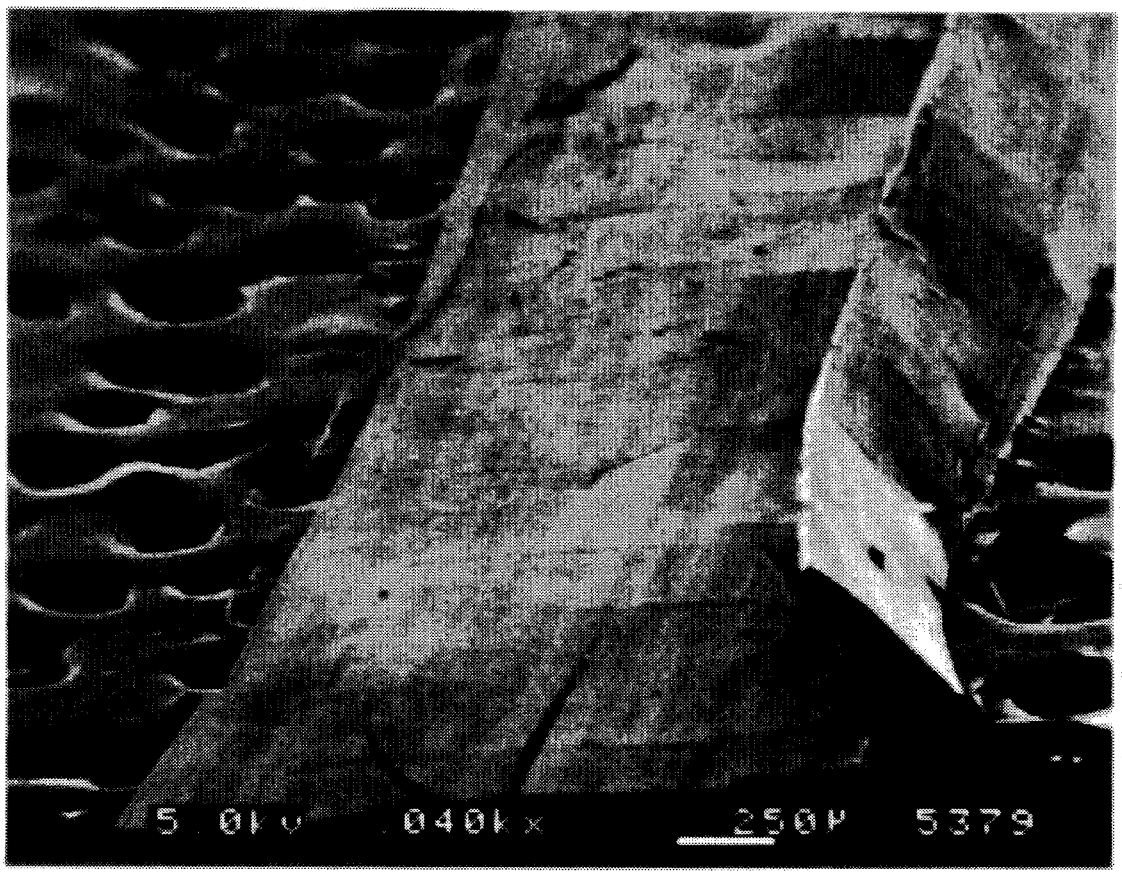
FIG. 4 is an SEM of a cross-section of another commercially available floss fiber enlarged 90 times.

FIG. 4 shows a conventional densified PTFE floss sold under the name EASY SLIDE. Again, this floss is folded upon itself to produce increased thickness and some limited degree of uniformity in dimensions.

The deficiencies of existing fibers as compared to the floss of the present invention can be demonstrated by a test of relative resistance to fibrillation between these fibers. A fibrillation resistance test was performed with existing floss fibers and the floss of the present invention which is outlined below. Both unwaxed and waxed samples were tested.

Figure 5:
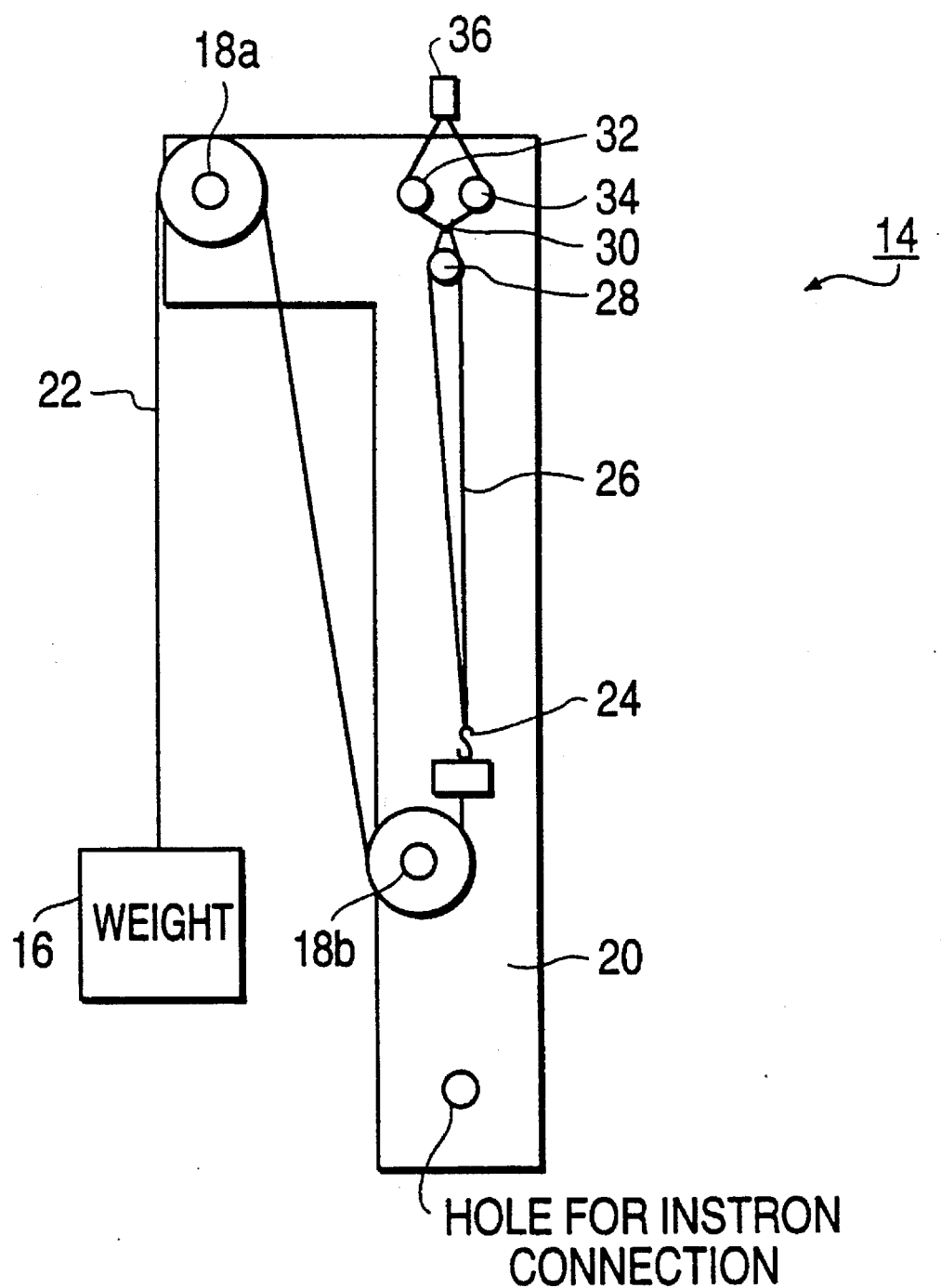
FIG. 5 is a schematic representation of apparatus used to test the fibrillation of the fibers of the present invention.

An apparatus 14 employed in the fibrillation resistance test is illustrated in FIG. 5. The apparatus 14 comprises a 900 gram weight 16 hung from a pulley system 18a, 18b attached to an L-shaped metal plate 20. One end of a string 22 holds the weight 16 while the other end is threaded through the pulley system 18a, 18b and tied to an S-hook 24. The S-hook 24 anchors the fiber to be tested and incorporates the weight into the system. The center of a 60 cm fiber segment 26 to be tested is looped around the S-hook 24. The fiber then is extended upward around a rod 28 (see above). A half hitch knot 30 is tied over the rod 28 and each fiber segment is separated and fed around rod 32 and rod 34, which are above rod 28. The two fiber ends meet and are wrapped around fiber grips 36 of an INSTRON machine. The test begins as the top INSTRON grip 36 moves upward and runs until the S-hook 24 reaches the rod 28 which corresponds to 12.5 cm of travel.

Careful monitoring of the fiber is performed through an illuminated 1.1× magnifying glass during testing. The fibers were judged to pass or fail the fibrillation test. To pass the test, there must be no apparent fibrillation. Failure occurred if at least one hair or pill was present after a single test run.

Testing was conducted on waxed samples of the inventive fiber, GLIDE® Floss, COLGATE PRECISION™ floss, and EASY SLIDE floss. Unwaxed samples of the inventive fiber and GLIDE® Floss were also run. Seven runs of each fiber was performed. The 900 gram load was kept constant for all fibers, waxed and unwaxed. The INSTRON cross head speed was 25.4 cm/minute. The type of knot tied was a half hitch knot, and the orientation was kept constant as left under right.

Figure 6:
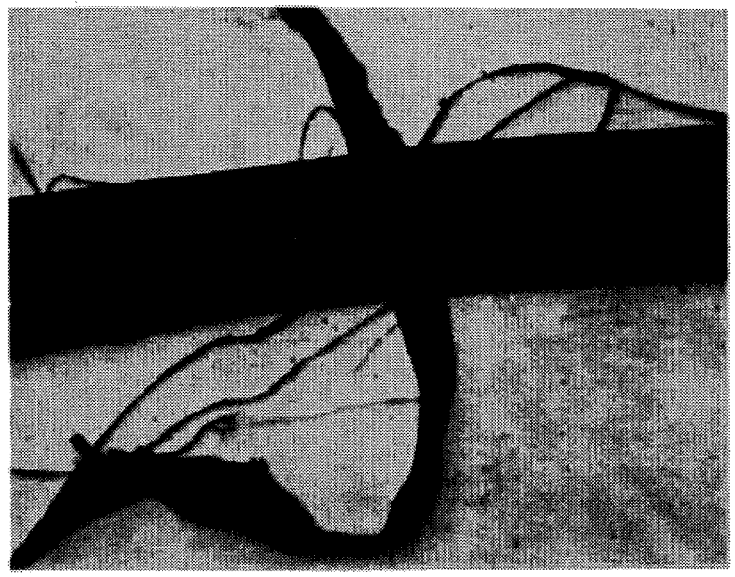
FIG. 6 is a photograph of a fiber of conventional floss enlarged 50 times, showing a failure in a fibrillation test.
Figure 7:
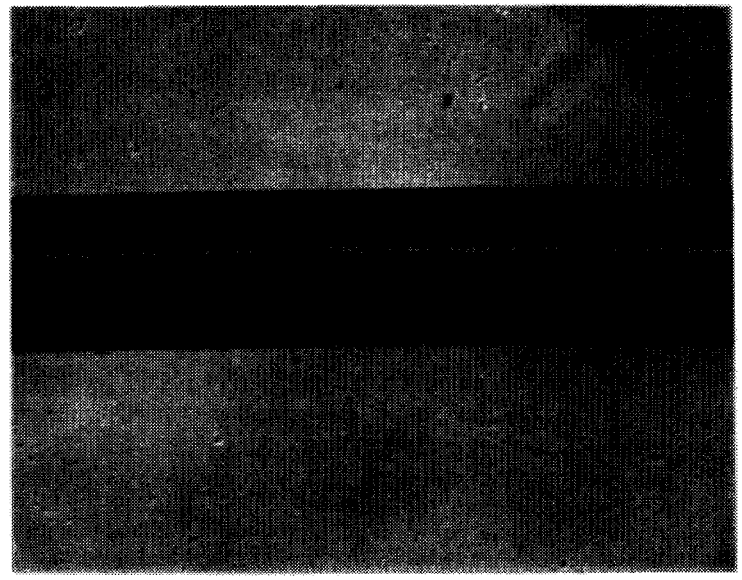
FIG. 7 is a photograph of a fiber of the present invention enlarged 50 times, showing no fibrillation following a fibrillation test.

Examples of the condition of fibers following the test are shown in the photographs of FIGS. 6 and 7. FIG. 6 illustrates a conventional waxed expanded PTFE fiber following the above described test. As can be seen, the fiber experienced noticeable fibrillation along its edges. By contrast, FIG. 7 shows a fiber of the present invention. As can be seen, no edge separation or fibrillation was detected.

The cumulative test results are outlined below.

| Comparative Fibrillation Testing Results - Waxed Fibers | | | | |
|---|---|---|---|---|
| Fiber | Results | | Fiber | Results |
| Waxed Fiber | | | | |
| 1 Inventive Fiber | Pass | 1 | GLIDE ® floss | Fail |
| 2 Inventive Fiber | Pass | 2 | GLIDE ® floss | Fail |
| 3 Inventive Fiber | Pass | 3 | GLIDE ® floss | Fail |
| 4 Inventive Fiber | Pass | 4 | GLIDE ® floss | Fail |
| 5 Inventive Fiber | Pass | 5 | GLIDE ® floss | Fail |
| 6 Inventive Fiber | Pass | 6 | GLIDE ® floss | Fail |
| 7 Inventive Fiber | Pass | 7 | GLIDE ® floss | Fail |
| 1 Easy Slide | Fail | 1 | Precision ™ | Fail |
| 2 Easy Slide | Fail | 2 | Precision ™ | Fail |
| 3 Easy Slide | Fail | 3 | Precision ™ | Fail |
| 4 Easy Slide | Fail | 4 | Precision ™ | Fail |
| 5 Easy Slide | Fail | 5 | Precision ™ | Fail |
| 6 Easy Slide | Fail | 6 | Precision ™ | Fail |
| 7 Easy Slide | Fail | 7 | Precision ™ | Fail |
| Unwaxed Fiber | | | | |
| 1 Inventive Fiber | Pass | 1 | GLIDE ® floss | Fail |
| 2 Inventive Fiber | Fail | 2 | GLIDE ® floss | Fail |
| 3 Inventive Fiber | Pass | 3 | GLIDE ® floss | Fail |
| 4 Inventive Fiber | Pass | 4 | GLIDE ® floss | Fail |
| 5 Inventive Fiber | Pass | 5 | GLIDE ® floss | Fail |
| 6 Inventive Fiber | Pass | 6 | GLIDE ® floss | Fail |
| 7 Inventive Fiber | Pass | 7 | GLIDE ® floss | Fail |

The results indicate that there exists a highly significant difference between the fibrillation resistance of the inventive floss and that of the other flosses tested. Using a one-way analysis of variance, the inventive floss has a 93%±6 probability of not fibrillating over the other flosses tested. The inventive floss fibrillated only one time out of fourteen times tested as compared to the other flosses which fibrillated in all cases.

The fiber of the present invention was also tested to determine its degree of uniformity as compared with existing PTFE fiber materials. The dimensions of the fibers were determined through the following procedure:

1. A random place on the fibers length was selected on the fiber by unwinding the fiber off its spool or core.
2. After selecting a starting point at random, the largest and smallest width within a 1 meter section of the random starting point was determined. The width was measured using a magnifying eyepiece having a mm scale of 0.1 mm resolution.
3. This procedure was repeated by selecting another random starting point and repeating step 2.
4. Repeat step 3 until 32 random lengths have been sampled
5. Compute the Delta Width Percent by the following formula.

$$\textit{Delta Width Percent} = \{2*(\textit{Max. Width} - \textit{Min. Width})/(\textit{Max. Width} + \textit{Min. Width})\}*100$$

Figure 8:
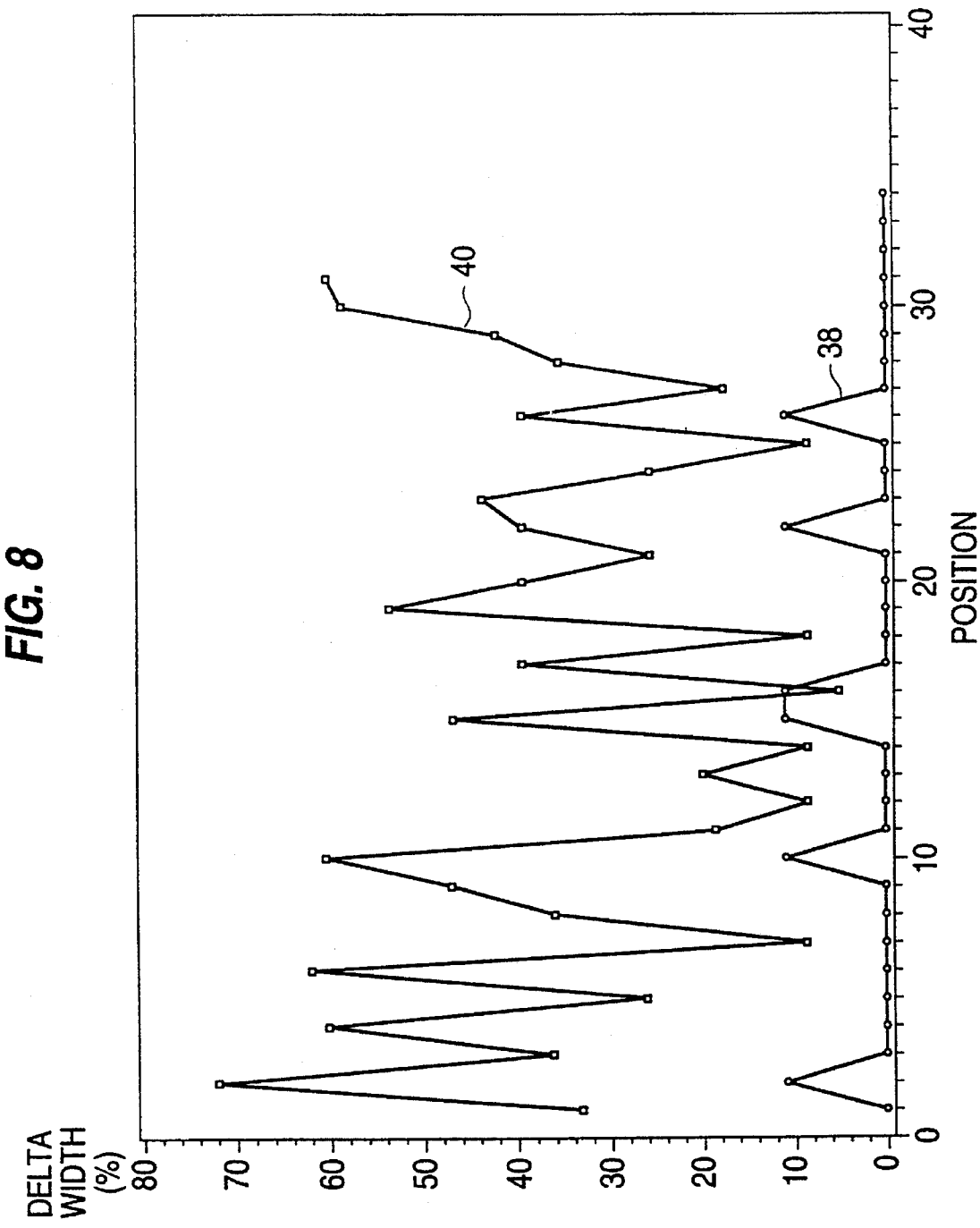
FIG. 8 is a graph of the uniformity of width of the floss of the present invention as compared with an existing PTFE floss.

FIG. 8 is a graph that demonstrates the width uniformity of the inventive floss 38 in comparison with a folded GLIDE® floss fiber 40. The variable Delta Width Percent is the computed subtraction of the smallest width from the largest width found over a one meter section randomly selected along the fiber's length and dividing this by the average of these minimum and maximum values and multiplying this quantity by one hundred.

The fiber of the present invention was also tested to determine its degree of thickness uniformity as compared with existing PTFE fiber materials. The thickness dimensions of the fibers were determined through the following procedure:

1. Start at a random place on the fiber's length by selecting a point on the fiber by unwinding the fiber off its spool or core.
2. After selecting a starting point at random, find the largest and smallest thickness within a 50 cm section (at least ten measurements must be taken) starting from the random starting point. Measure the thickness using a snap gauge having a precision of 0.0001 inch (2.54 μm).
3. Continue by selecting another random starting point and repeat step 2.
4. Repeat step 3 until ten random lengths have been sampled.
5. Compute the Delta Thickness Percent by the following formula.

*Delta Thickness Percent={2\*(Max. Thickness−Min. Thickness)/ (Max. Thickness+Min. Thickness}\*100*

Figure 9:
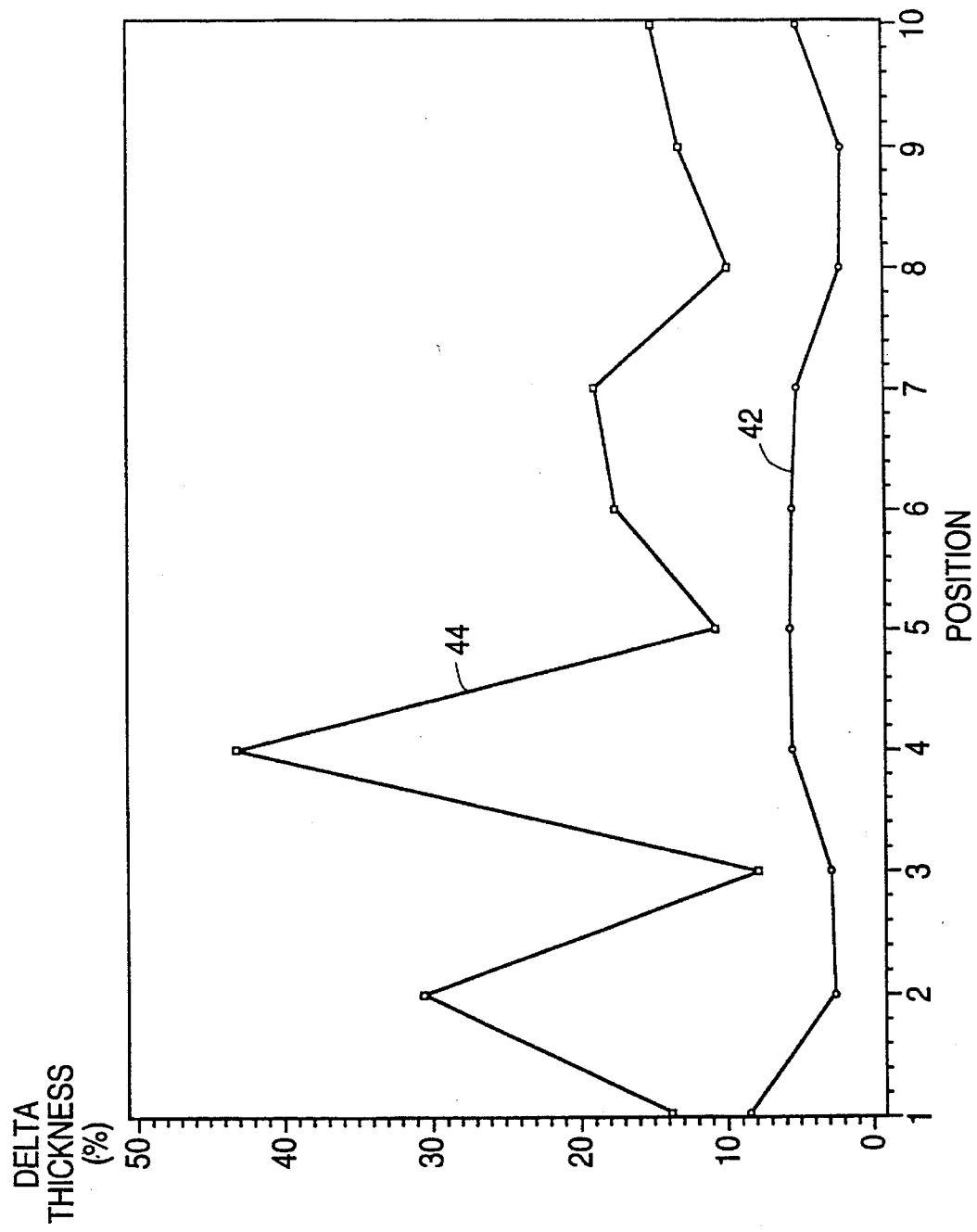
FIG. 9 is a graph of the uniformity of thickness of the floss of the present invention as compared with an existing PTFE floss.

FIG. 9 is a graph that demonstrates the thickness uniformity of the inventive floss 42 in comparison with folded GLIDE® floss fiber 44. The variable Delta Thickness Percent is the computed subtraction of the smallest thickness from the largest thickness found over a 50 cm section randomly selected along the fiber's length and dividing this by the average of these minimum and maximum values and multiplying this quantity by one hundred.

The wide degree of variance in width and thickness measured on the GLIDE® floss demonstrates the inconsistent results inherent with folded floss processing. The above described test demonstrates that the floss of the present invention is significantly more uniform in both width and thickness than the best available PTFE floss materials. FIG. 8 depicts that in general, the floss of the present invention will vary in width only 0 to 15% along its length over a one meter sample. Preferably, the floss of the present invention will vary in width less than 11% along its length over a one meter sample. FIG. 9 depicts that in general the floss of the present invention will vary in thickness only 2 to 15% along a 50 cm length. Preferably, the floss of the present invention will vary in thickness less than 9% along a 50 cm length. "Uniform" is meant to describe floss which varies approximately 15% or less in width or thickness according to the test described above.

The floss of the present invention has many improved properties over any previous floss material. First, it has increased uniform dimensions along its length which, among other things, provides more uniform flossing performance, denotes quality, and is aesthetically pleasing. Second, the floss of the present invention exhibits increased porosity or "void content." The void content is measured by the ratio of the article's bulk density to its intrinsic density. When processed in the manner described, it has been found that the floss of the present invention remains quite porous and compressible in its completed form and has the ability to densify under low stress. This property makes the floss easier to handle and more comfortable when applied between teeth and gums.

Figure 10:
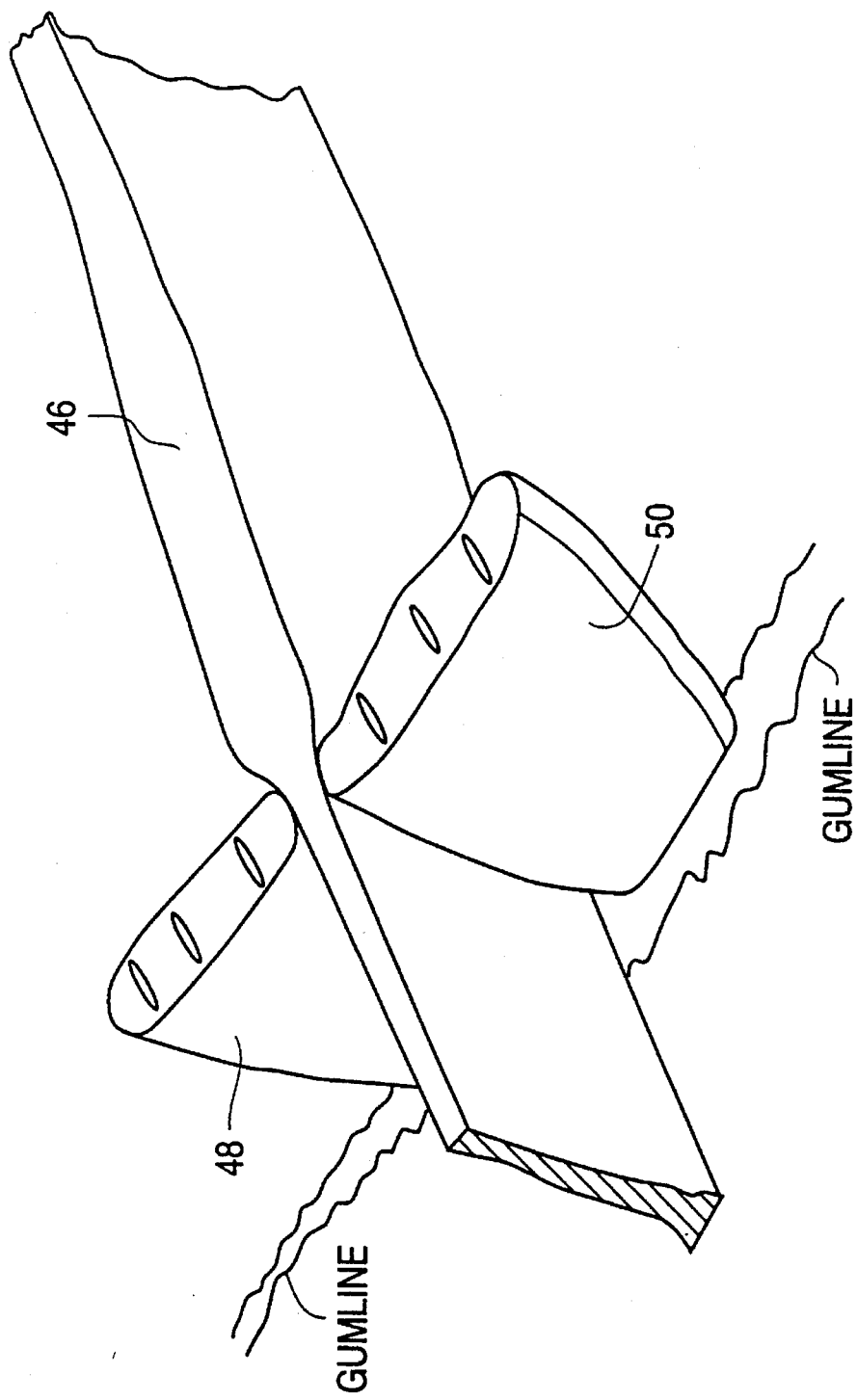
FIG. 10 is a partially schematic representation of a floss fiber of the present invention compressing while passing through a tight contact between two teeth.

As a result, the floss will densify when squeezed through a tight area, such as when passed between teeth during flossing. As is shown in FIG. 10, when a floss 46 of the present invention is passed between teeth 48, 50 in a conventional manner, the floss conforms to the contour of the gap between the teeth and densities in the process. This is believed to produce a signficantly better cleaning action than that possible with conventional flosses by wiping across a greater portion of the area of the teeth.

While the unused floss has an opaque white color, following flossing the length of floss used will densify to a remarkably different transparent or translucent color. This property is not as evident in other expanded PTFE flosses, perhaps due to visual interference caused by the folding of the floss.

The change in color of the floss after use provides a number of important enhancements to the floss. First, this provides an automatic indication of those areas of floss that have been used and densified. This simplifies the process of advancing the floss after use and assures that fresh floss can be used between each tooth. Second, it has long been a desire to include active agents, such as sodium fluoride or antibiotics, in a floss to provide direct topical application to the teeth and/or gums below the gum line. One problem with this approach remains that there has not been a reliable mechanism for determining exactly where and how much of the active ingredients have been applied. It is believed that the floss of the present invention can provide a ready marking of which segments of floss have been used and the amount of such use.

As has been explained, one of the exciting properties of the floss of the present invention is its high degree of compressibility when compared with existing expanded PTFE flosses. In order to quantify this property, the following procedure was performed on two conventional floss fibers as compared to a floss fiber made in accordance with the present invention:

1. A piece of fiber was cut approximately 25 cm in length from each spool of fiber;
2. The thickness of the fiber was measured over several regions of the sample using a snap gauge accurate to 0.0001 inch (25.4 μm) and the average thickness [$T_i$] was computed. In the case of folded fibers, the fiber was carefully unfolded before measuring the thickness. The fiber's thickness is defined below;
3. The fiber was placed on a smooth non yielding surface;
4. Using a smooth convex tool, the fiber's thickness was compressed by rubbing the convex portion of the tool against the fiber's width area stroking the tool back and forth along its length. Using hand pressure of approximately 7 kg, approximately 20–40 strokes over a 4 cm portion of a 130 tex fiber are required to fully compress the fiber over the 4 cm region. One immediate indication as to whether sufficient pressure is being applied is found by looking at the expanded PTFE fiber's color change. When appropriate pressure is applied, the ePTFE fiber will change from a white opaque color to a clear-translucent color;
5. The compressed thickness of the fiber was measured using the snap gauge (to 0.0001" (25.4 μm) precision) at several regions over the compressed fiber and the average compressed thickness [$T_c$] was computed;
6. The percent compression was computed using the following formula:

*% Compression=$(1-T_c/T_i)$\*100*

Experimental Results:

| Sample | $T_i(\sigma)$ inch | $T_c(\sigma)$ inch | % Compress |
|---|---|---|---|
| Inventive floss | 0.00365 (.00016) | 0.00185 (.0002) | 49.3 |
| GLIDE ® floss | 0.00126 (.00005) | 0.00079 (.00007) | 37.3 |
| EASY SLIDE from J & J | 0.00093 (.00006) | 0.00078 (.00016) | 16.0 |

As can be observed, the inventive floss has a significantly improved degree of compressibility over any existing floss products. The above test demonstrates that inventive floss is shown to have greater compressibility than GLIDE® floss and J&J's EASY SLIDE floss; greater by 24% and 68% respectively. It is believed that the floss of the present invention will regularly experience a degree of compressibility of between 20 and 60% under the above described test, with a typical compressibility in excess of 40% being expected.

The degree of compressibility of the floss of the present invention not only improves its feel and flossing properties, but is further believed to improve its handling properties. It is believed that the use of the floss of the present invention improves the ability to grip the floss, making its handling far easier. For instance, a typical PTFE floss is coated with 3.5 to 10% by weight of wax or other material to aid in its handling. It has been discovered that nearly identical handling characteristics can be provided with a coating of only 2 to 3% by weight of wax. For most applications, it is believed that the wax content need not exceed 3% by weight.

Another important property of the floss of the present invention is its improved surface properties. One measure of the surface of the floss is its surface roughness.

Surface roughness was tested using a non contact optical interferometric profiler capable of measuring step-heights from 100 angstroms to 100 micrometers on the Z-axis and surface roughness to greater than several micrometers. The instrument used for the testing was the model WYKO RST Surface/Step Tester which is available from WYKO Corporation, Tucson, Ariz.

The parameters for the interferometer follow: a 10× objective was used for the surface roughness analysis which provides profiles over a 422 μm×468 μm area and has a spacial sampling interval of 1.9 μm. A white light-single source with beam splitting was the source used during testing on the interferometer.

Below is a table outlining the surface roughness of several PTFE fibers characterized by peak to valley ratio, average roughness and root mean square (RMS) along each fiber's surface on the width dimension.

| | Inventive Fiber | | GLIDE ™ | | J & J EasySlide |
|---|---|---|---|---|---|
| Measurement | Wax μm | Unwax μm | Wax μm | Unwax μm | Wax μm |
| Ra | 3.43 | 1.27 | 2.72 | 21.58 | 3.11 |
| Ra = Average Roughness | | | | | |
| Rq | 4.37 | 1.72 | 3.31 | 25.07 | 3.77 |
| Rq = Root Mean Square | | | | | |
| Rt | 31.9 | 15.56 | 18.01 | 84.93 | 22.62 |
| Rt = Peak to Valley | | | | | |
| SA | 1.061 | 1.017 | 1.009 | 1.037 | 1.013 |
| SA Index = Scanned Area (400 × 400 μm)/Surface Area | | | | | |

The inventive unwaxed fiber is shown to have a smoother surface than the other fibers. This smoother surface characteristic is believed to aid in the fibrillation resistance of the fiber.

Another embodiment of a floss of the present invention is by the incorporation either by a coating (lick or dip), impregnation, and or coextrusion of at least one active ingredient such as an anti-microbial, antibiotic, antibacterial agents, antifungal, dentifrice, remineralizing agents, whitening agents, immunological agents, anti-tartar, anti-caries agents, anti-plaque agents, lysozmes, anti-inflammatory agents, hemostatic agents, analgesics and mixtures thereof. At least one of the following materials can be added to the floss of the present invention such as: sodium fluoride, zinc chloride, tetrasodium pyrophosphate, sodium acid pyrophosphate, tetrapotassium pyrophosphate, vitamin K, water soluble calcium salts, blood factors that initiate the coagulation cascade, aminocaproic acid, tranexamic acid, adrenaline, alum, noradrenaline, iron salts and calcium alginate, sodium monofluorophosphate, stannous fluoride, chlorhexidine, hexachlorophene, cetyl pyridinium chloride, benzethonium chloride, ureases, calcium carbonate, magnesium carbonate, othophosphoric acid, monosodium phosphate, monopotassium phosphate, disodium phosphate, dipotassium phosphate, hemisodium phosphate, benzothonium, chloride, acetyl trimethyl ammonium bromide, sanguinaria, triclosan, tetracycline, cety pyridinium chloride, benzothonium chloride, melt emulsion of dimethicone and mixtures thereof.

The advantage of placing or adding active agents or ingredients to the floss of the present invention is the expected uniform control of active agent or ingredient delivery to the areas which are exposed to the floss during flossing such as the area of the gum which comes into contact with the floss during flossing. The cross-sectional uniformity of the inventive floss permits a controlled release of the active ingredient/agent over a determined length of floss during floss use. This controlled release or delivery of the active ingredient/agent is a result of the support surface being of uniform surface area along the length of the article. The uniform area is the result of the consistent width of the article. Since the active agent is released from the surface of the inventive floss, the amount of active agent being released is a function of surface area which comes into contact with the applied surface such as the area between the teeth of the floss user, it is critical then that the contact area be consistent such to yield in a consistent release of the active agent to the applied area. If the support surface or structure is not uniform such as found in a support surface or structure of varying width such as a folded article, then the amount of active ingredient/agent being released during flossing will also vary, thus leading to the dilemma of questioning the quantity of active ingredient which actually is released during floss use.

Another advantage to the embodiment of a floss of the present invention is by the incorporation either by a coating (lick or dip), impregnation, and or coextrusion of at least one of the above active ingredients is that the floss of the present invention is not folded thus minimizing the chance for active ingredients being inhibited for releasement due to being caught in a fold.

There exists advantages as well of the present invention for the embodiment of the incorporation of active ingredients since the present invention is very hydrophobic, water based (which is desired for solubility in salvia) active ingredients will tend to remain on the surface of the inventive article and not be soaked into the cross-section of the inventive article thereby permitting the releasement of the active agent(s) from the surface relatively easily through mechanical means done by moving or sliding the inventive article through the user's teeth and scraping the active agent(s) off from the inventive article and placing the active agent in the salvia as well as on the teeth which are the scraping surfaces.

There exists additional advantages as well of the present invention for the embodiment of the incorporation of active ingredients since the present invention is very porous (similar to a sponge), active ingredients having surface tensions below ≈30 Dynes/cm @23° C. can easily be soaked or impregnated into the cross-section of the inventive article thereby permitting the releasement of the active agent(s) from the inside region of the inventive floss through its surface relatively easily through mechanical means done by compressing or squeezing the inventive article through the user's teeth during use of the inventive article done by moving or sliding the inventive article and scraping the active agent(s) off from the inventive article and placing the active agent in the salvia as well as on the teeth which are the compressing and scraping surfaces.

Without intending to limit the scope of the present invention, the following examples illustrate how the present invention may be made and used:

EXAMPLE 1

A fiber of the present invention was produced in the following manner.

A fine powder PTFE resin was combined in a blender with an amount of an odorless mineral spirit (Isopar K available from Exxon Corporation) until a compound was obtained. The volume of mineral spirit used per gram of fine powder PTFE resin was 0.264 cc/g. The compound was compressed into a billet and extruded through a 0.64 mm gap die attached to a ram type extruder to form a coherent extrudate. A reduction ratio of 85:1 was used.

Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 6.0 mm widths by passing it between a set of gapped blades. The slit coherent extrudate was expanded uniaxially in the longitudinal direction over hot plates at a temperature of 325° C. at a total ratio of 30 to 1 to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.1 mm |
| Thickness: | 0.089 mm |
| Weight/Length: | 131 tex |
| Density: | 1.34 g/cc |
| Tensile strength: | 3600 g |
| Tenacity: | 27.5 g/tex |

EXAMPLE 2

A fiber of the present invention was produced in the following manner.

A coherent extrudate was produced in the same manner as in Example 1. Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 5.1 mm widths by passing it between a set of gapped blades. The slit coherent extrudate was expanded uniaxially in the longitudinal direction over hot plates at a temperature of 335° C. at a total ratio of 13 to 1 to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.3 mm |
| Thickness: | 0.130 mm |
| Weight/Length: | 253 tex |
| Density: | 1.50 g/cc |
| Tensile strength: | 4630 g |
| Tenacity: | 18.3 g/tex |

EXAMPLE 3

A fiber of the present invention was produced in the following manner.

A coherent extrudate was produced in the same manner as in Example 1. Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 6.9 mm widths by passing it between a set of gapped blades. The slit coherent extrudate was expanded uniaxially in the longitudinal direction over hot plates at a temperature of 335° C. at a total ratio of 43 to 1 to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.2 mm |
| Thickness: | 0.069 mm |
| Weight/Length: | 137 tex |
| Density: | 1.67 g/cc |
| Tensile strength: | 4450 g |
| Tenacity: | 32.5 g/tex |

EXAMPLE 4

A fiber of the present invention was produced in the following manner.

A coherent extrudate was produced in the same manner as in Example 1. Subsequently, the odorless mineral spirit was volatilized and removed, and the dry coherent extrudate was expanded uniaxially in the longitudinal direction 1.9 times its original length by passing the dry coherent extrudate over a series of rotating heated rollers at a temperature of 275° C. The dry coherent expanded extrudate was slit to 5.1 mm widths by passing it between a set of gapped blades. The slit coherent extrudate was expanded uniaxially in the longitudinal direction over hot plates at a temperature of 335° C. at a total ratio of 26 to 1 to form a fiber. This fiber was subsequently subjected to an amorphous locking step by passing the fiber over a heated plate set at a temperature of 400° C. for about 1 second.

The following measurements were taken on the finished fiber:

| | |
|---|---|
| Width: | 1.0 mm |
| Thickness: | 0.091 mm |
| Weight/Length: | 128 tex |
| Density: | 1.40 g/cc |
| Tensile strength: | 3590 g |
| Tenacity: | 28.0 g/tex |

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A dental floss having a length, width, and thickness, comprising:

a single expanded polytetrafluoroethylene (PTFE) fiber having a density of 1.0 to 1.9 g/cc and uniform dimensions of width and thickness along its length and having an outer surface of essentially rectangular to oblong cross-sectional dimension, the single fiber being without folds so that its outer surface is fully exposed;

wherein the floss has essentially parallel exposed edges and the edges are resistant to fibrillation during use.

2. The dental floss of claim 1 wherein the width of the floss is at least 0.5 mm and the thickness of the floss is at least 50 μm.

3. The dental floss of claim 1 wherein the floss comprises dimensions of at least 0.7 mm in width and at least 50 μm in thickness.

4. The dental floss of claim 1 wherein the fiber has sufficient porosity to allow the fiber to compress to at least 40% of its original thickness.

5. The dental floss of claim 4 wherein the fiber undergoes a color change between an uncompressed state and a compressed state, providing indication of segments of floss that have been used.

6. The dental floss of claim 5 wherein the fiber changes from a white color to translucent upon compression.

7. The dental floss of claim 1 wherein the fiber is sufficiently porous so as to undergo a color change after use.

8. The dental floss of claim 1 wherein the floss is coated with a wax, the total wax content being less than 3% by weight of the floss.

9. A dental floss of claim 1 wherein the floss incorporates at least one active ingredient.

10. The dental floss of claim 9 wherein the active ingredient is selected from the group consisting of at least one of an anti-microbial, antibiotic, antibacterial agents, antifungal, dentifrice, remineralizing agents, whitening agents, immunological agents, anti-tartar, anti-caries agents, anti-plaque agents, lysozmes, anti-inflammatory agents, hemostatic agents, analgesics.

11. A dental floss of claim 9 wherein at least one active ingredient is impregnated into the cross-section of the inventive article.

12. The dental floss of claim 1 wherein the PTFE material possesses a void content between 13 and 55%.

13. A dental floss comprising a single strand of expanded polytetrafluoroethylene (PTFE) fiber, the PTFE fiber having a density of 1.0 to 1.9 g/cc and being of uniform dimensions in width along its entire length;

wherein the single fiber in an unfolded orientation comprises a width of at least 0.5 mm and a thickness of at least 50 μm; and wherein the fiber is maintained in an unfolded orientation for use as a floss.

14. The dental floss of claim 13 wherein the floss is coated with a wax, the wax content being less than 3% by weight of the floss.

15. The dental floss of claim 13 wherein the floss is porous and compressible.

16. The dental floss of claim 15 wherein the floss undergoes a change in color after use.

17. The dental floss of claim 16 wherein the floss changes from a white color to translucent upon compression.

18. The dental floss of claim 13 wherein the fiber has sufficient porosity to allow the fiber to compress to at least 40% of its original thickness.

19. The dental floss of claim 13 wherein the floss has essentially parallel exposed edges and the edges are resistant to fibrillation during use.

20. A method for producing an improved floss that comprises providing a sheet of expanded porous polytetrafluoroethylene (PTFE), the sheet having a thickness of at least 50 μm;

slitting the PTFE sheet into multiple strands of PTFE fibers, each strand comprising a single fiber of at least 0.5 mm in width and 50 μm in thickness and having a density of 1.0 to 1.9 g/cc and substantially uniform dimensions along its length;

winding the PTFE fibers onto a spool, substantially maintaining the strands in a flat, unfolded orientation.

21. The method of claim 20 further comprising prior to winding onto the spool, coating the PTFE fibers with a layer of wax, the total quantity of wax applied being less than 3% by weight of the floss.

22. The method of claim 20 further comprising producing a final floss product with a width of 0.5 to 3.0 mm and a thickness of 50 to 250 μm.

23. The method of claim 20 further comprising producing a final floss product with a PTFE void content between 13 and 55%.

24. The method of claim 20 that further comprises following slitting of the sheet into strands, further expanding the strands to the desired final dimensions.

25. A dental floss having a length, width, and thickness, comprising:

an expanded polytetrafluoroethylene (PTFE) fiber having uniform dimensions of width and thickness along its length and having an outer surface of essentially rectangular to oblong cross-sectional dimension, the fiber being without folds so that its outer surface is fully exposed;

wherein the floss has essentially parallel exposed edges and the edges are resistant to fibrillation during use;

wherein the floss has sufficient porosity to allow the fiber to compress to at least 40% of its original thickness; and wherein the floss undergoes a color change between an uncompressed state and a compressed state, providing indication of segments of floss that have been used.

26. The dental floss of claim 25 wherein the floss undergoes a color change from a white color to translucent upon compression.

27. A dental floss comprising
a strand of expanded polytetrafluoroethylene (PTFE) fiber, the PTFE fiber being of uniform dimensions in width along its entire length;
wherein the fiber in an unfolded orientation comprises a width of at least 0.5 mm and a thickness of at least 50 µm;
wherein the fiber is maintained in an unfolded orientation for use as a floss; and
wherein the dental floss is porous and compressible, the floss undergoing a change in color from white to translucent upon compression.

* * * * *